United States Patent
Klewinghaus (10) Patent No.: US 11,857,711 B2
(45) Date of Patent: Jan. 2, 2024

(54) METHOD FOR SETTING A CONTROL DEVICE OR A CLOSED-LOOP CONTROL DEVICE OF A BLOOD TREATMENT APPARATUS, AND DEVICES

(71) Applicant: Fresenius Medical Care Deutschland GmbH, Bad Homburg (DE)

(72) Inventor: Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 456 days.

(21) Appl. No.: 16/981,453

(22) PCT Filed: Mar. 14, 2019

(86) PCT No.: PCT/EP2019/056414
§ 371 (c)(1),
(2) Date: Sep. 16, 2020

(87) PCT Pub. No.: WO2019/175306
PCT Pub. Date: Sep. 19, 2019

(65) Prior Publication Data
US 2021/0046235 A1 Feb. 18, 2021

(30) Foreign Application Priority Data
Mar. 16, 2018 (DE) ..................... 10 2018 106 254.0

(51) Int. Cl.
*A61M 1/16* (2006.01)
*A61M 1/34* (2006.01)
(Continued)

(52) U.S. Cl.
CPC ............ *A61M 1/1601* (2014.02); *A61M 1/28* (2013.01); *A61M 1/34* (2013.01); *A61M 60/113* (2021.01); *A61M 2205/3334* (2013.01)

(58) Field of Classification Search
CPC .............. A61M 1/1601; A61M 1/1603; A61M 1/1613; A61M 1/28; A61M 1/34;
(Continued)

(56) References Cited

U.S. PATENT DOCUMENTS

| 6,602,424 B1 | 8/2003 | Kramer et al. |
| 2016/0121037 A1 | 5/2016 | Golarits et al. |
| 2016/0354528 A1* | 12/2016 | Pouchoulin ......... A61M 1/3413 |

FOREIGN PATENT DOCUMENTS

| CN | 105561415 | 5/2016 |
| EP | 2762179 | 2/2017 |

(Continued)

OTHER PUBLICATIONS

Kindgen-Milles, "Akutes Nierenversagen: Die Behandlung des akuten Nierenversagens mit kontinuierlichen Nierenersatzverfahren," Fresenius Medical Care, 2012, 73 pages (with English version).
(Continued)

*Primary Examiner* — John Kim
(74) *Attorney, Agent, or Firm* — Fish & Richardson P.C.

(57) ABSTRACT

A method for setting a control device or a closed-loop control device of a blood treatment apparatus, includes providing, determining or reading out a correction factor and correcting the flow value and/or the treatment target entered by the user by or about the correction factor. Furthermore, the present disclosure relates to a blood treatment apparatus, a digital storage medium, a computer program product, and a computer program.

6 Claims, 4 Drawing Sheets

(51) Int. Cl.
*A61M 1/28* (2006.01)
*A61M 60/113* (2021.01)
(58) Field of Classification Search
CPC .. A61M 1/3403; A61M 1/341; A61M 60/113; A61M 2205/3334; A61M 2205/50
See application file for complete search history.

(56) References Cited

FOREIGN PATENT DOCUMENTS

WO     WO 03/028860     4/2003
WO     WO 2013/144793     10/2013

OTHER PUBLICATIONS

PCT International Preliminary Report on Patentability in International Appln. No. PCT/EP2019/056414, dated Oct. 1, 2020, 19 pages (with English translation).
PCT International Search Report and Written Opinion in International Appln. No. PCT/EP2019/056414, dated Jun. 27, 2019, 23 pages (with English translation).

* cited by examiner

METHOD FOR SETTING A CONTROL DEVICE OR A CLOSED-LOOP CONTROL DEVICE OF A BLOOD TREATMENT APPARATUS, AND DEVICES

CROSS-REFERENCE TO RELATED APPLICATIONS

The present application is the national stage entry of International Patent Application No. PCT/EP2019/056414, filed on Mar. 14, 2019, and claims priority to Application No. DE 10 2018 106 254.0, filed in the Federal Republic of Germany on Mar. 16, 2018, the disclosures of which are expressly incorporated herein in its entirety by reference thereto.

TECHNICAL FIELD

The present disclosure relates to a method for setting a control device or a closed-loop control device of a blood treatment apparatus for an upcoming blood treatment session. The disclosure further relates to a blood treatment apparatus, a digital storage medium, a computer program product, and to a computer program.

BACKGROUND

Some apparatuses for the extracorporeal blood treatment perform blood treatments and achieve predetermined targets by the end of the treatment session. Some apparatuses achieve the predetermined treatment target, specified at the beginning of the treatment, within a predetermined time period. For this purpose, treatment parameters like pump flows may be suitably set at the beginning of the treatment session. Furthermore, information about the target values which relate to certain blood parameters and/or to the treatment duration may be made in advance.

SUMMARY

Due to interruptions of the treatment session, for example, because of a bag change or because of medical examination of the patient, for which the patient must be separated from the treatment apparatus, it may happen that the treatment duration must be subsequently increased in order to achieve the sought or desired treatment target. Alternatively, complex regulations are conceivable which, during the ongoing treatment session, effect with high, in particular metrological effort settings made in advance, so that the treatment target given or contemplated in advance is achieved despite interruptions etc.

An object of the present disclosure is to specify a further method by which a desired treatment target may be achievable despite interruptions. In addition, a blood treatment apparatus is described which is suitable for executing the method. Furthermore, a suitable digital storage medium, a suitable computer program product and a suitable computer program for executing the method are to be specified.

In all of the following implementations, the use of the expression "may be" or "may have" and so on, is to be understood synonymously with "preferably is" or "preferably has," and so on respectively, and is intended to illustrate embodiments.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" as encompassing "at least one". This understanding is also equally encompassed as the interpretation that a numeric word, for example, "one" may alternatively mean "exactly one", wherever this is evidently technically possible for the person skilled in the art. Both are encompassed and apply herein to all used numerical words.

Whenever "programmed" or "configured" is mentioned herein, then it is also disclosed to interchange these terms.

The information "top" and "bottom" are herein to be understood in case of doubt by the person skilled in the art as absolute or relative spatial information, which refer to the orientation of the respective component when used as intended.

The method, relates to setting a control device or a closed-loop control device which is configured to control or control in a closed-loop manner (in short: to control) a blood treatment apparatus. The blood treatment apparatus to be controlled comprises a blood pump. The blood pump is connectable to an extracorporeal blood circuit and is designed to convey a fluid, in particular blood, through the extracorporeal blood circuit.

The blood treatment apparatus to be controlled optionally comprises a dialysis liquid inlet line and further optionally comprises a dialysis liquid pump. The optional dialysis liquid pump is designed to convey dialysis liquid through the dialysis liquid inlet line, in particular towards a blood filter when the blood treatment apparatus is in use.

The blood treatment apparatus to be controlled comprises further optionally an ultrafiltration pump for achieving an ultrafiltration and/or an effluent pump for discarding effluent (amongst others used dialysate).

The blood treatment apparatus to be controlled comprises an input device with which a user, e.g. clinic personnel or a doctor, may enter flow values, e.g. values of flow rates, which values should be achieved or effected during the upcoming blood treatment session using the blood pump and/or the dialysis liquid pump and/or the ultrafiltration pump and/or the effluent pump. Entering a treatment target, which should be achieved by the end of the upcoming blood treatment session, may take place alternatively to the entry of flow values or in addition thereto.

The weight of the patient may be required for deriving the flow rates to be set from the dose specification (ml/(kg×h)). This information may optionally also be entered prior to the treatment by the user to the blood treatment apparatus, e.g. using the input device.

The blood treatment apparatus to be controlled comprises a reading device for reading and/or storing the flow rates and/or the treatment target respectively entered by the user.

The blood treatment apparatus to be controlled comprises the a.m. control device or closed-loop control device. The latter is configured and/or prepared to control and/or to regulate the blood treatment apparatus after the start of the upcoming session based on flow values and/or regarding the desired or sought treatment target.

The blood treatment apparatus is suitable to be controlled or regulated by the method, wherein the method encompasses providing, determining or reading out a correction factor (alternatively: predetermined correction factor), and correcting by the correction factor the flow values and/or the treatment target, respectively entered by the user. The correction takes place preferably prior to the beginning of the treatment session. The correction preferably increases the set flow values and/or the treatment target (respectively its value or level), being entered by the user, by the correction factor.

The method encompasses providing, determining or reading out a correction factor (alternatively: predetermined correction factor) and correcting by the correction factor the flow values and/or the treatment target, respectively entered by the user. The correction takes place preferably prior to the beginning of treatment session. The correction preferably increases the set flow values and/or the treatment target (or its value or level), being entered by the user, by the correction factor.

The blood treatment apparatus to be controlled by the method, comprises a blood pump. This blood pump is connectable to an extracorporeal blood circuit and is designed to convey fluid, in particular blood, through the extracorporeal circuit.

The blood treatment apparatus optionally comprises an optional dialysis liquid inlet line and further optionally a dialysis liquid pump. The optional dialysis liquid pump is configured to convey dialysis liquid through the dialysis liquid inlet line, in particular towards a blood filter, when the blood treatment apparatus is in use.

The blood treatment apparatus comprises an input device with which the user, e.g. clinic personnel or a doctor, may enter or input flow values, e.g. values of flow rates, which values should be achieved or effected during the upcoming blood treatment session using the blood pump and/or the dialysis liquid pump and/or the ultrafiltration pump and/or the effluent pump. Entering a treatment target, which should be achieved by the end of the upcoming blood treatment session, may take place alternatively to the entry of flow values or in addition thereto.

The blood treatment apparatus comprises a reading device for reading and/or storing the flow rates and/or the treatment target respectively entered by the user.

The blood treatment apparatus comprises the a.m. control device or closed-loop control device. The latter is configured and/or prepared to control and/or to regulate the blood treatment apparatus after the start of the upcoming session based on flow values and/or regarding the desired or sought treatment target.

The blood treatment apparatus further comprises a storage device.

The blood treatment apparatus is suitable to be controlled or regulated by the method, wherein the method encompasses providing, determining or reading out a correction factor (alternatively: predetermined correction factor), and correcting by the correction factor the flow values and/or the treatment target, respectively entered by the user. The correction takes place preferably prior to the beginning of treatment session. The correction preferably increases the set flow values and/or the treatment target (respectively its value or level), being entered by the user, by the correction factor.

A digital, in particular non-volatile, storage medium, in particular in the form of a machine-readable carrier, in particular in the form of a floppy disk, CD, DVD or an EPROM, in particular with electronically or optically readable control signals, can interact with a programmable computer system such that the machine-induced steps of the method are prompted.

A computer program product comprises a program code volatile or saved on a machine-readable storage carrier or a signal wave for prompting the machine-induced steps of the method when the computer program product runs on a computer. A computer program product can be understood as, for example, a computer program which is stored on a carrier, an embedded system as a comprehensive system with a computer program (for example, an electronic device with a computer program), a network of computer-implemented computer programs (for example, a client-server system, a cloud computing system, etc.) or a computer on which a computer program is loaded, running, saved, executed or developed.

The blood treatment apparatus is suitable to be controlled or regulated by the method, wherein the method encompasses providing, determining or reading out a correction factor (alternatively: 50 correction factor), and correcting by the correction factor the flow values and/or the treatment target, respectively entered by the user. The correction takes place preferably prior to the beginning of the treatment session. The correction preferably increases the set flow values and/or the treatment target (respectively its value or level), being entered by the user, by the correction factor.

A computer program comprises a program code for prompting the machine-induced steps of the method when the computer program runs on a computer, a computer program can be understood as, for example, a physical, ready-for-distribution software product, which comprises a program.

It is applicable for the digital storage medium, the computer program product and the computer program that all, several or some of the machine-induced steps of the method are prompted. This applies particularly in interaction with a detecting device and/or with a blood treatment apparatus as described herein.

Embodiments may comprise one or several of the features mentioned above or in the following. In this, the features mentioned herein may, in any combination, be subject-matter of embodiments, unless the person skilled in the art recognizes a specific combination as technically impossible.

Whenever an embodiment is mentioned herein, it is then an exemplary embodiment.

In several embodiments, a blood treatment session is only considered as such only when the patient is connected to the blood treatment apparatus, e.g. by the blood hose system, when blood has been withdrawn from the patient and/or when blood is returned to the patient, in neither case not before.

The correction factor may be an empirical value which may result from practice and the daily routines in the respective clinic of the user. Thus, for example, a waiting time for a bag change may take different lengths, since the bags to be replaced have to be brought over long distances in the one clinic, whereas they are stored near the apparatus in the other clinic.

The correction factor may be determined by the targeted analysis of previous blood treatment sessions of the same treatment regimen performed in the same clinic or care unit and stored e.g. in the machine control system of the blood treatment apparatus.

Such analysis of previous blood treatment sessions may be automatically carried out by the machine control system of the blood treatment apparatus in certain blood treatment apparatuses, in particular adaptive blood treatment apparatuses. With that, an improved correction factor may be advantageously achieved and also automatically set or proposed for setting to the user. In particular activities taking place as scheduled, like bag change, may be considered in the evaluation of the standstills of the system which cause a reduction of the actually administered dose compared with the set treatment dose or the desired treatment target (flows or dose settings).

In several embodiments, the entered correction factor is subjected to a plausibility check, for example by the reading device or another device programmed for this purpose. This enables to check whether a correction factor, respectively its value, entered by the user is plausible for the specific application. Corresponding criteria may be stored, for example in the storage device. The criteria may differ depending on the type of blood treatment, its initially set duration, the specific patient, the category or class of patients to which the patient belongs (side-diseases, age, mobility, etc.) etc. The plausibility check is considered as passed for example if the correction factor, possibly related to the specific patient or the patient category, meets the criterion or the criteria.

In some embodiments, a predetermined correction factor is entered and used instead of the correction factor. Herein, everything regarding the correction factor also applies unchanged to the lead factor.

In several embodiments, a value range (limited on both sides or limited on one side, such as by a threshold) is entered or specified, within which the entered correction factor has to lie. Should the user want to make inputs outside this range of values, then the reading device or another device programmed for this purpose may prevent this and/or output a display or warning to the user.

In some embodiments, the control device or the closed-loop control device comprises a routine for the plausibility check of the correction factor, which routine serves for preventing senseless values from being entered at all, e.g. by specifying an upper and/or lower limit or a value range for the correction factor beyond or outside of which an entry is not possible.

In some embodiments, a device, e.g. the control device and/or closed-loop control device, calculates the correction factor or adapts an entered correction factor automatically. For this purpose, it may refer to e.g. relevant pump values, the sum of the late absences (of the patient) which are already known at the beginning of the treatment, e.g. the temporary absence of the patient due to scheduled medical examinations, target flow during the absence periods or the expected running time of the pumps, etc. For this purpose, it may, in particular automatically, additionally or alternatively use values, times or time periods and/or at least one observation from previous treatment sessions of the same patient or a collection of patients.

In several embodiments, the method is not executed after the beginning of the treatment session.

In several embodiments, the treatment target is a treatment result relative or over the treatment duration.

Figure 2:
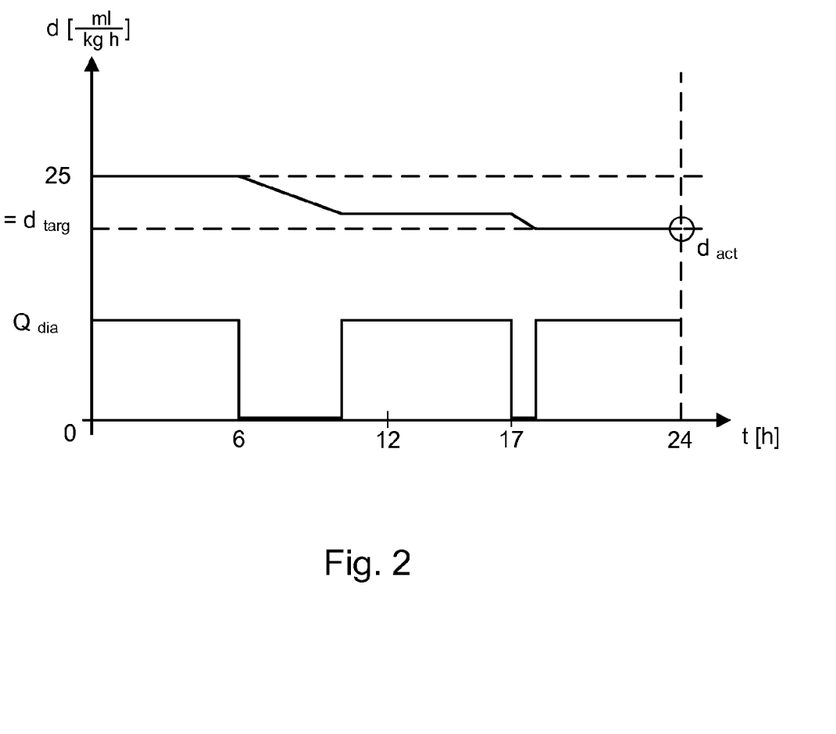
FIG. 2 exemplarily shows a graphic illustration of the 24-hour course of a blood treatment session without using the method.

An example of a treatment result is the treatment dose in the dialysis or the dialysis dose, which is given as a value having the dimension [ml/kg*h], see also FIG. 2.

In some embodiments, the correction factor of the method is stored as a constant in the storage device and may be provided by and/or read out from it.

In several embodiments, the correction factor stored as a constant in the storage device must be adapted by specially authorized persons, e.g. authorized clinic personnel and/or an authorized technician, in case changes thereon are desired. In these embodiments, the user is not capable or authorized to do so.

In certain embodiments, the correction factor or the control value respectively the constant may be based on empirical values, as already stated supra.

In some embodiments, the correction factor or the control value may be calculated or may have been calculated based on possible and/or scheduled interruptions in the blood treatment course.

In certain embodiments, in particular within the scope of extracorporeal blood treatment methods with regional citrate anticoagulation, the correction factor may affect also a citrate rate via the blood pump rate when a dosage of citrate solution is carried out automatically and proportional to the blood flow rate.

Furthermore, in some embodiments, applying the correction factor on the dialysate rate may indirectly also affect the calcium rate, in particular when the latter depends on the effluent rate as usual. Usually, the effluent rate depends on the net ultrafiltration rate and also on the dialysate rate and citrate rate. Especially for the mode of action of the regional citrate anticoagulation it is advantageous that the correction factor is equally applied to both parameters (blood rate and dialysate rate) so as not to change their relationship to each other. Otherwise, an unintentional shift in the patient's acid-base state could occur.

Adapting, in particular increasing the net ultrafiltration rate or the ultrafiltration rate by the ultrafiltration pump should preferably also be done by the correction factor as well. This may be provided in some embodiments.

In certain embodiments, applying the correction factor on or to the dialysate rate may indirectly increase the effluent rate, as the flowing dialysate is herewith also needed.

In several embodiments, the correction factor is between 10% and 30%, in particular between 15% and 25%, especially particularly at 20%. Alternatively or additionally, the correction of the entered flow rates and/or of the treatment target entered by the user is in a range between 10% and 30%, in particular between 15% and 25%, especially particularly about 20%. The previous percent information relates to at least one, several (arbitrary and in arbitrary combinations) or all flow values entered by the user and/or to the treatment target entered by the user (respectively its value or level).

In some embodiments, the correction value of the method is being or has been entered by the user, e.g. a doctor or clinic personnel, using the input device.

In certain embodiments, the blood treatment apparatus is designed as a peritoneal dialysis apparatus, hemodialysis apparatus, hemofiltration apparatus or hemodiafiltration apparatus, in particular as an apparatus for chronic renal replacement therapy or continuous renal replacement therapy (CRRT).

Some or all of the embodiments may possess one, several or all of the aforementioned and/or following advantages.

With the aid of the method, it is advantageously possible to avoid an increased metrological effort of using complex sensor technology for regulating and controlling of pump systems of the blood treatment apparatus. This effort would be necessary as an alternative to the procedure described herein if one wanted to enable the blood treatment apparatus to achieve a treatment target even if the blood treatment session should be interrupted. The control device could make a target/actual comparison between what was achieved until the interruption and what is sought to be achieved until end of the treatment session and regulate the blood treatment apparatus after the interruption accordingly (which is not required and is therefore omitted in several embodiments). However, this requires a relatively high metrological effort. This metrological effort has so far resulted in higher hardware costs and an increased validation effort for the device software. With the method, the effort required for this purpose and the associated costs may advantageously be reduced or avoided.

Since the method is easy to implement and also easy to install, for example by a simple software update, this advantageously offers the retrofitting of existing devices.

Advantageously, error-prone sensor technology for controlling the correction is omitted within the scope of the method, which may lead to a simpler and maintenance-free operation of the blood treatment apparatus and/or course of the blood treatment.

Another advantage of the method is that its automation does not allow the user to forget steps required to compensate the treatment backlog caused by or due to the interruption of the treatment session. An interruption of the treatment session may be, for example, a bag change or medical examination of the patient, for which the patient must be separated from the treatment apparatus. The method may adjust the treatment duration in order to achieve the sought or desired treatment target. The method may result in an achieved treatment target (given or contemplated in advance) despite interruptions.

In addition, no calculation errors may occur in the course of the treatment, in particular due to the use of control factors which are predetermined and possibly already checked for plausibility, which in turn increases the safety of the patient.

Finally, it is advantageous that the user no longer needs to worry about a correction. It may be sufficient for him for example to set the treatment target to a familiar value or quantity.

Any necessary corrections may be done instead by the control device, e.g. through reading out, determining and/or considering the correction factor, presumably even with a higher quality than the user might be able to.

BRIEF DESCRIPTION OF THE DRAWINGS

The present invention is exemplarily explained below with regard to the accompanying drawings in which identical reference numerals refer to the same or similar components. The following applies.

DETAILED DESCRIPTION OF THE FIGURES

Figure 1:
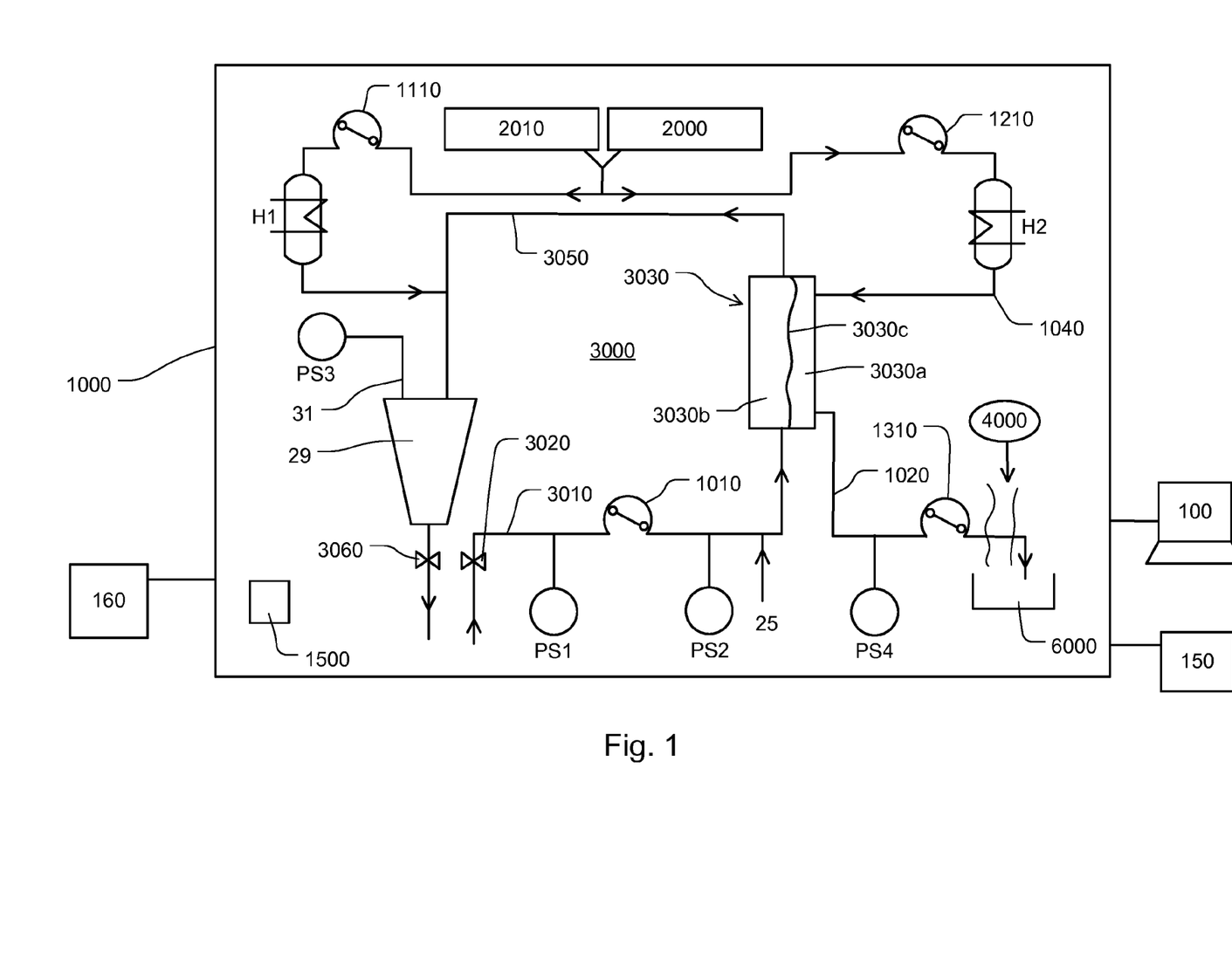
FIG. 1 shows a simplified illustration of an embodiment of a blood treatment apparatus having an extracorporeal blood circuit.

FIG. 1 shows a greatly simplified illustration of a blood treatment apparatus 1000, connected to an extracorporeal blood circuit 3000 and to an only roughly indicated discharge hose system having an optional effluent bag 4000. The extracorporeal blood circuit 3000 comprises a first line 3010, herein in the form of an arterial line section.

The first line 3010 is in fluid communication with a blood treatment device, herein a blood filter or dialyzer 3030 by way of example. The blood filter 3030 comprises a dialysis liquid chamber 3030a and a blood chamber 3030b, which are separated from each other by a mostly semi-permeable membrane 3030c.

The extracorporeal blood circuit 3000 further comprises at least a second line 3050, herein in the form of a venous line section or a return line. Both the first line 3010 and the second line 3050 may serve for connection to the vascular system of the patient who is not illustrated.

The first line 3010 is optionally connected to a (first) hose clamp 3020 for blocking or closing the line 3010. The second line 3050 is optionally connected to a (second) hose clamp 3060 for blocking or closing the line 3050.

The blood treatment apparatus 1000 which is represented, only by some of its devices and merely schematically, in FIG. 1, comprises a blood pump 1010. During the patient's treatment the blood pump 1010 conveys blood through sections of the extracorporeal blood circuit 3000 and towards the blood filter or dialyzer 3030. This is indicated by the small arrow tips, which are used in FIG. 1 to generally illustrate the direction of flow Fresh dialysis liquid is pumped from a source 2000 along the dialysis liquid inlet line 1040 into the dialysis liquid chamber 3030a, by a pump 1210 for dialysis liquid, which may be designed as a roller pump or as an otherwise occluding pump. The dialysis liquid leaves the dialysis liquid chamber 3030a in the direction of the basin 6000, as dialysate possibly enriched by filtrate, and is herein referred to as effluent.

The source 2000 may be, for example a bag or a container. Further, the source 2000 may also be a fluid line from which the online and/or continuously generated or mixed liquid is provided, for example a hydraulic outlet or connection of the blood treatment apparatus 1000.

A further source 2010 with substitute may be optionally provided. It may correspond to the source 2000 or be a separate source.

At the bottom right of FIG. 1 is indicated where the discharge hose system with the effluent bag 4000 is connected to the blood treatment apparatus 1000.

In addition to the aforementioned blood pump 1010, the arrangement in FIG. 1 further comprises purely optionally a series of further pumps, in each case optional, namely the pump 1110 for substitute, the pump 1210 for dialysis liquid and the pump 1310 for the effluent.

The pump 1210 is provided to supply dialysis liquid, from a source 2000, for example a bag, via an optional existing bag heater with a bag H2 to the blood filter 3030, via a dialysis liquid inlet line 1040.

The thus supplied dialysis liquid exits from the blood filter 3030 via a dialysate outlet line 1020, supported by the pump 1310, and may be discarded.

Upstream of blood pump 1010 an optional arterial sensor PS1 is provided. During the patient's treatment it measures the pressure in the arterial line.

Downstream of the blood pump 1010, but upstream of the blood filter 3030 and if provided, upstream of a coupling site 25 for heparin, a further optional pressure sensor PS2 is provided. It measures the pressure upstream of the blood filter 3030 ("pre-hemofilter").

Another further pressure sensor may be provided as PS4 downstream of the blood filter 3030, however preferably upstream of the pump 1310, in the dialysate outlet line 1020 to measure the filtrate pressure of the blood filter 3030.

Blood, which leaves the blood filter 3030, passes through an optional venous blood chamber 29, which may comprise a deaeration device 31 and which may be in fluid communication with a further pressure sensor PS3.

A control device or a closed-loop control device 1500 for controlling or regulating the blood treatment apparatus 1000 may be provided and may be in signal communication and/or control communication with all the a.m. components of the blood treatment apparatus 1000.

Furthermore, an input device 100, a reading device 150 and a storage device 160 are connected to the blood treatment apparatus 1000 in signal communication and/or control communication.

FIG. 2 shows a treatment result d (in [ml/kg*h]) over the time t (in [h]) upon completion of a common blood treatment session set for 24 hours for the acute treatment of the patient with two interruptions starting after 6 hours respectively after 17 hours. The interruptions can each be recognized by the drop of $Q_{dia}$. $Q_{dia}$ corresponds to the flow of the dialysis pump 1210. Other pump flows, for instance $Q_B$ for the blood pump 1010, $Q_{UF}$ for the ultrafiltration pump or flows of the effluent pump may as well be affected by the interruptions.

The treatment result is also affected by both interruptions: d decreases further upon and during each interruption. This would require a regulating mechanism in order to achieve the desired treatment result $d_{targ}$ of 25 ml/kg*h until the completion or the end of the predetermined 24 hours.

As can be seen in FIG. 2, the set treatment target $d_{targ}$ is not reached after 24 hours due to both interruptions, because the actual achieved treatment result $d_{act}$ is less than dtarg.

Figure 3:
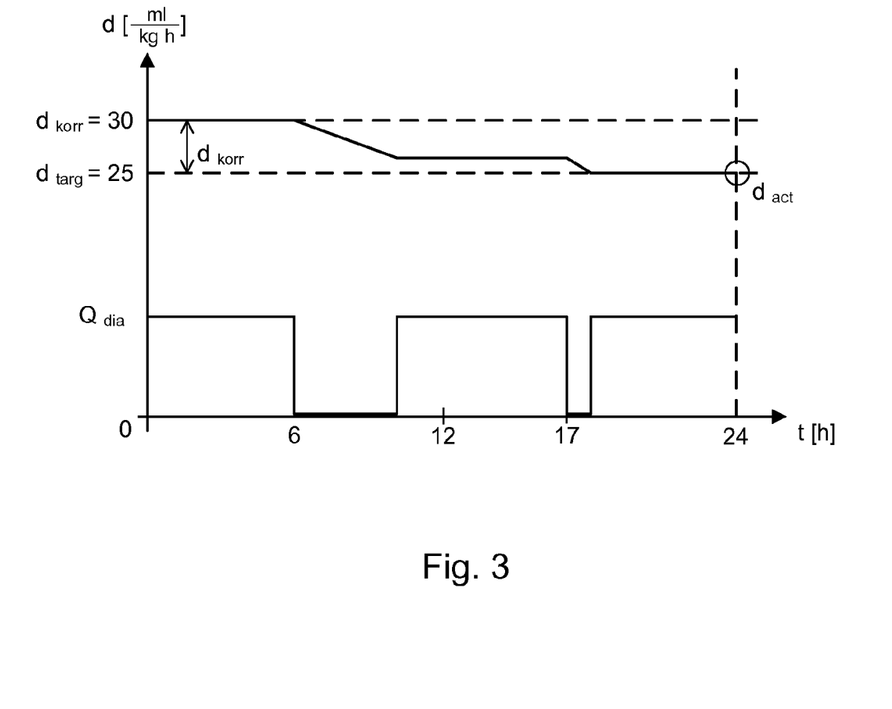
FIG. 3 shows a graphic illustration of the 24-hour course of a blood treatment session with an exemplary embodiment of the method.

FIG. 3 shows the course of a blood treatment session with the same interruptions like in FIG. 2, herein however by using an exemplary embodiment of the method. The treatment target was automatically corrected upwards already before the beginning of the treatment session, i.e. at t less than or equal to 0, by a correction factor (here exemplarily by 20%). Pump flows and/or other machine parameters were raised to the new, higher, corrected treatment target $d_{korr}$. Based thereon, the set, initial treatment target is achieved after 24 hours; $d_{targ}=d_{act}$ applies.

Figure 4:
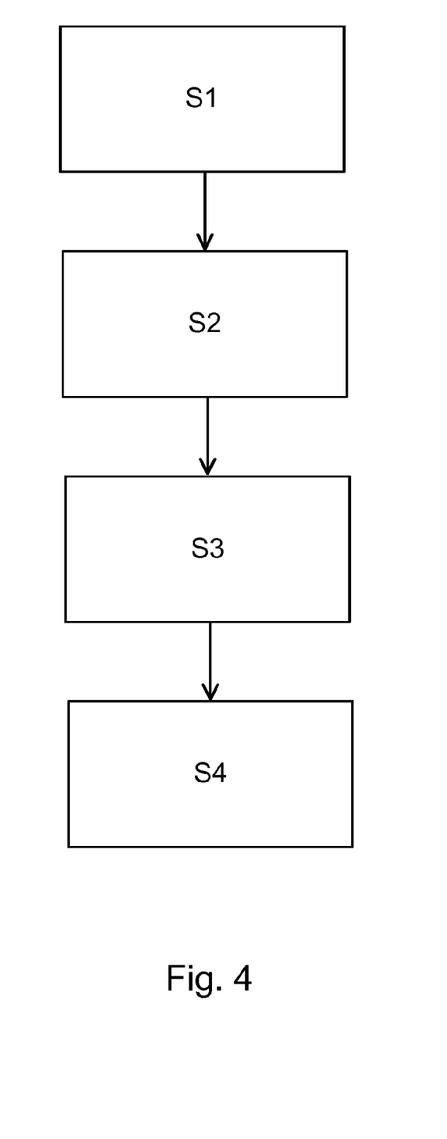
FIG. 4 shows the course of an exemplary embodiment of the method in a flow diagram.

FIG. 4 shows the course of an exemplary embodiment of the method in a flow diagram.

In this, S1 describes the input of the correction factor $f_{korr}$ or the reading out thereof from the storage device 160.

The step S2 describes the setting of the initial value $d_{korr}$ taking into consideration the correction factor $f_{korr}$, added to the treatment target $d_{targ}$.

Step S3 represents the running treatment over 24 hours, with interruptions of the treatment session.

Step S4 represents achieving the treatment target $d_{targ}$ at the end of the 24-hour treatment session, wherein preferably $d_{act}=d_{targ}$ is achieved.

LIST OF REFERENCE NUMERALS

25 addition site for heparin (optional)
29 venous blood chamber
31 deaeration device
100 input device
150 reading device
160 storage device
1000 blood treatment apparatus
1010 blood pump
1020 dialysate outlet line, effluent inlet line
1040 dialysis liquid inlet line
1110 pump for substitute
1210 dialysis liquid pump
1310 pump for dialysate or effluent
1500 control device or closed-loop control device
2000 dialysis liquid source
2010 substituate source, optional
3000 extracorporeal blood circuit
3010 first line (arterial line section)
3020 (first) hose clamp
3030 blood filter or dialyzer
3030a dialysis liquid chamber
3030b blood chamber
3030c semi-permeable membrane
3050 second line (venous line section)
3060 (second) hose clamp
4000 effluent bag
6000 basin
H2 bag heating with bag (dialysis liquid)
H1 bag heating with bag (substituate)
PS1, PS2 arterial pressure sensor (optional)
PS3 venous pressure sensor (optional)
PS4 pressure sensor for measuring the filtrate pressure
$d_{act}$ actually reached treatment result
$d_{targ}$ set treatment target
$d_{korr}$ corrected treatment target
$f_{korr}$ correction factor, predetermined correction factor
$Q_{dia}$ dialysis liquid pump flow
$Q_B$ blood pump flow
$Q_{UF}$ ultrafiltration pump flow

The invention claimed is:

1. A blood treatment apparatus comprising:
a blood pump, connectable to an extracorporeal blood circuit and configured to convey blood through the extracorporeal blood circuit;
a dialysis liquid inlet line;
a dialysis liquid pump configured to convey dialysis liquid through at least one of the dialysis liquid inlet line, an ultrafiltration pump flow, and an effluent pump;
an input device configured to receive at least one of a flow value to be achieved or effected during an upcoming blood treatment session and a treatment target to be achieved by the completion of the upcoming blood treatment session, wherein the at least one of the flow value and the treatment target is achieved or effected by at least one of the blood pump, the dialysis liquid pump, the ultrafiltration pump flow, and the effluent pump;
a reading device configured to read and store the at least one of the flow value and the treatment target;
a storage device, wherein a predetermined correction factor is stored as a constant on the storage device; and
a control device configured to control or regulate the blood treatment apparatus after a start of the upcoming blood treatment session based on the at least one of the flow value and the treatment target; wherein the control device is configured to execute a method comprising:
a) providing, from the storage device, the predetermined correction factor; and
b) correcting the at least one of the flow value and the treatment target received by the input device using the predetermined correction factor stored on the storage device.

2. The blood treatment apparatus according to claim 1, wherein the treatment target is a treatment outcome or result relative to or over a treatment duration.

3. The blood treatment apparatus according to claim 1, wherein the predetermined correction factor is between 10% and 30%.

4. The blood treatment apparatus according to claim 1, wherein the predetermined correction factor effects a correction between 10% and 30% of the at least one of the flow value and the treatment target.

5. The blood treatment apparatus according to claim 1, wherein the input device is configured to receive the predetermined correction factor from a user of the blood treatment apparatus.

6. The blood treatment apparatus according to claim 1, wherein the blood treatment apparatus is a peritoneal dialysis apparatus, a hemodialysis apparatus, a hemofiltration apparatus, a hemodiafiltration dialysis apparatus, a chronic renal replacement therapy apparatus, or a continuous renal replacement therapy apparatus.

* * * * *